(12) United States Patent
Yagi et al.

(10) Patent No.: US 10,076,729 B2
(45) Date of Patent: Sep. 18, 2018

(54) MIXING DEVICE, MIXING TUBE, DRUG SOLUTION INJECTING SYSTEM, AND DRUG SOLUTION MIXING METHOD

(71) Applicant: NEMOTO KYORINDO CO., LTD., Tokyo (JP)

(72) Inventors: Takanobu Yagi, Tokyo (JP); Young Kwang Park, Tokyo (JP); Mitsuo Umezu, Musashino (JP)

(73) Assignee: NEMOTO KYORINDO CO., LTD., Tokyo (JP)

( * ) Notice: Subject to any disclaimer, the term of this patent is extended or adjusted under 35 U.S.C. 154(b) by 222 days.

(21) Appl. No.: 15/062,256

(22) Filed: Mar. 7, 2016

(65) Prior Publication Data
US 2016/0250605 A1    Sep. 1, 2016

Related U.S. Application Data

(63) Continuation of application No. 13/639,814, filed as application No. PCT/JP2011/001812 on Mar. 28, 2011, now Pat. No. 9,314,749.

(30) Foreign Application Priority Data

Apr. 5, 2010   (JP) .................................. 2010-087017

(51) Int. Cl.
*B01F 5/00* (2006.01)
*A61J 1/20* (2006.01)
(Continued)

(52) U.S. Cl.
CPC .............. *B01F 5/0068* (2013.01); *A61J 1/20* (2013.01); *A61K 49/005* (2013.01);
(Continued)

(58) Field of Classification Search
CPC ...... A61J 1/20; A61M 2206/16; A61M 5/007; A61M 5/19; A61M 5/008; B01F 3/0865; B01F 5/0057; B01F 5/0068; B01F 5/0074
(Continued)

(56) References Cited

U.S. PATENT DOCUMENTS 4,855,066 A    8/1989  Petty et al.
4,931,225 A *  6/1990  Cheng ................ B01D 19/0005
                                              261/76
(Continued)

FOREIGN PATENT DOCUMENTS

DE        3227884 A1    2/1983
JP        55-076025 U   5/1980
(Continued)

OTHER PUBLICATIONS

The first Office Action issued by the Chinese Patent Office dated Sep. 5, 2016, which corresponds to Chinese Patent Application No. 201410401247.4 and is related to U.S. Appl. No. 15/062,256; with English language translation.
(Continued)

*Primary Examiner* — Deanna K Hall
(74) *Attorney, Agent, or Firm* — Studebaker & Brackett PC

(57) ABSTRACT

To provide a mixing device, a mixing tube, a drug solution injecting system, and a drug solution mixing method capable of evenly and efficiently mixing a plurality of kinds of drug solutions. The mixing device according to the present invention includes: a swirling flow generating chamber; a first inflow opening for introducing a first drug solution into the swirling flow generating chamber in a direction parallel to a central axis of the swirling flow; a second inflow opening for introducing a second drug solution into the swirling flow generating chamber so as to generate a swirling flow of the
(Continued)

second drug solution having a specific gravity lower than that of the first drug solution; an outflow opening for discharging a mixed drug solution; and a narrowing chamber which is interposed between the swirling flow generating chamber and the outflow opening and has a space continuously narrowed toward the outflow opening.

15 Claims, 13 Drawing Sheets

(51) Int. Cl.
  *A61M 5/00* (2006.01)
  *A61M 5/145* (2006.01)
  *A61M 5/168* (2006.01)
  *B01F 3/08* (2006.01)
  *A61K 49/00* (2006.01)
  *A61M 5/19* (2006.01)
  *A61M 39/22* (2006.01)

(52) U.S. Cl.
  CPC ......... *A61K 49/0071* (2013.01); *A61M 5/007* (2013.01); *A61M 5/14546* (2013.01); *A61M 5/14566* (2013.01); *A61M 5/16827* (2013.01); *A61M 5/19* (2013.01); *B01F 3/0865* (2013.01); *B01F 5/0057* (2013.01); *A61M 39/223* (2013.01); *A61M 2206/16* (2013.01); *B01F 2215/0032* (2013.01)

(58) Field of Classification Search
  USPC .......................................................... 604/82
  See application file for complete search history.

(56) References Cited

U.S. PATENT DOCUMENTS

| | | | |
|---|---|---|---|
| 5,409,610 A | 4/1995 | Clark | |
| 7,018,451 B1 | 3/2006 | Torkildsen et al. | |
| 7,553,294 B2 * | 6/2009 | Lazzaro | A61M 5/14546 604/131 |
| 7,670,315 B2 * | 3/2010 | Cowan | A61M 5/007 600/432 |
| 7,771,383 B2 | 8/2010 | Truitt et al. | |
| 8,715,222 B2 | 5/2014 | Truitt et al. | |
| 2005/0051917 A1 | 3/2005 | Grothe et al. | |
| 2014/0257198 A1 | 9/2014 | Truitt et al. | |

FOREIGN PATENT DOCUMENTS

| | | |
|---|---|---|
| JP | 58-017824 A | 2/1983 |
| JP | 03-045691 A | 2/1991 |
| JP | 05-337352 A | 12/1993 |
| JP | 2008-517653 A | 5/2008 |
| JP | 2009-101329 A | 5/2009 |
| JP | 2009-247404 A | 10/2009 |
| WO | 2007/116840 A1 | 10/2007 |

OTHER PUBLICATIONS

An Office Action; "Notification of Reasons for Refusal" issued by the Japanese Patent Office dated Jul. 20, 2016, which corresponds to Japanese Patent Application No. 2015-135854 and is related to U.S. Appl. No. 15/062,256; with English language translation.
International Search Report; PCT/JP2011/001812; dated Jun. 14, 2011.
Written Opinion of the International Searching Authority; PCT/JP2011/001812; dated Jun. 14, 2011.

* cited by examiner

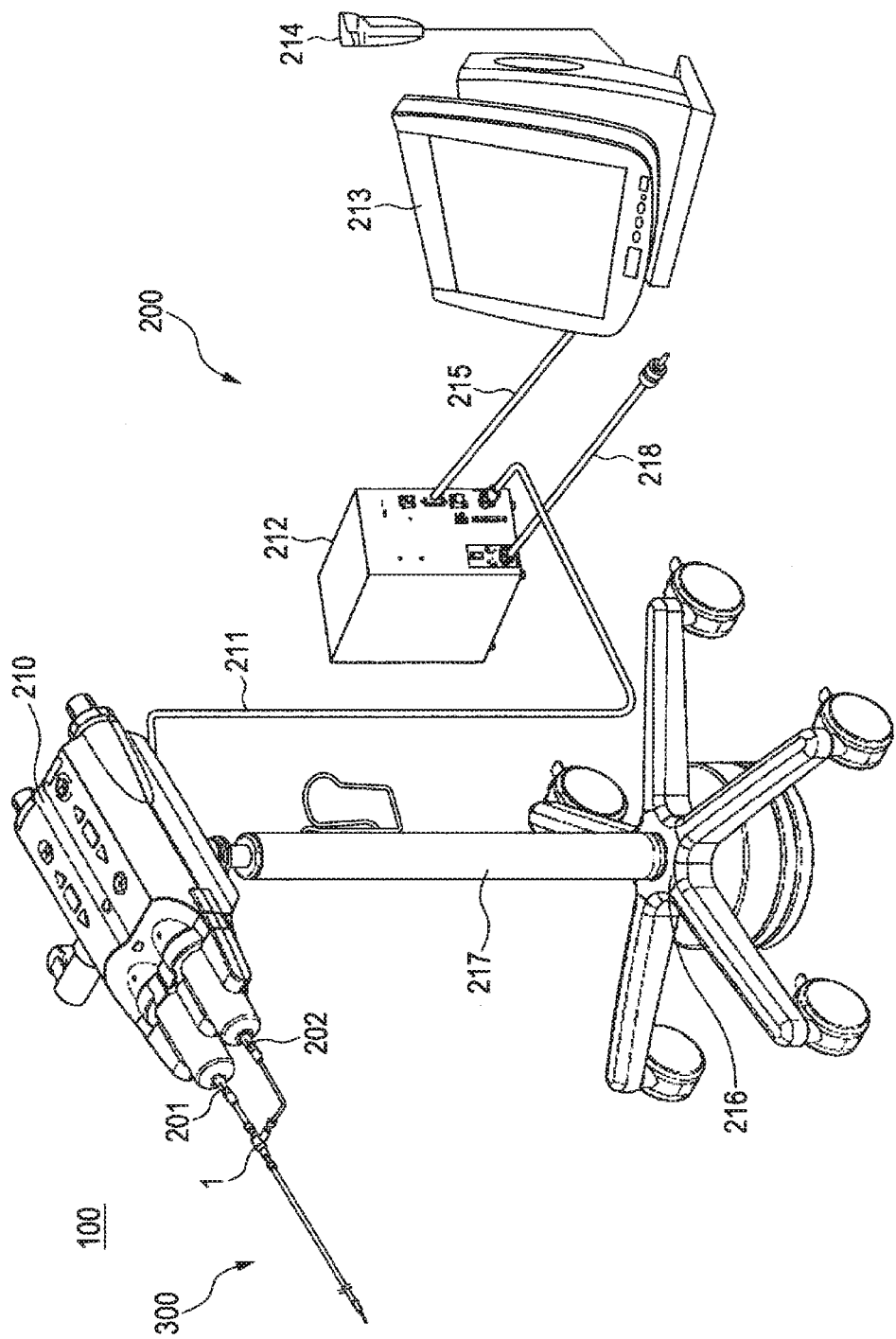
[Fig. 1]

[Fig. 2]
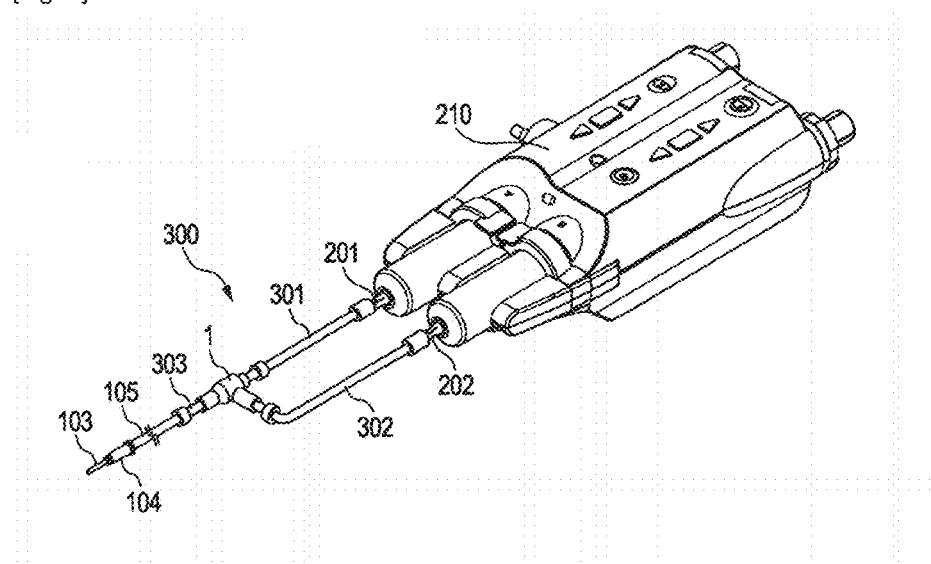
[Fig. 3]
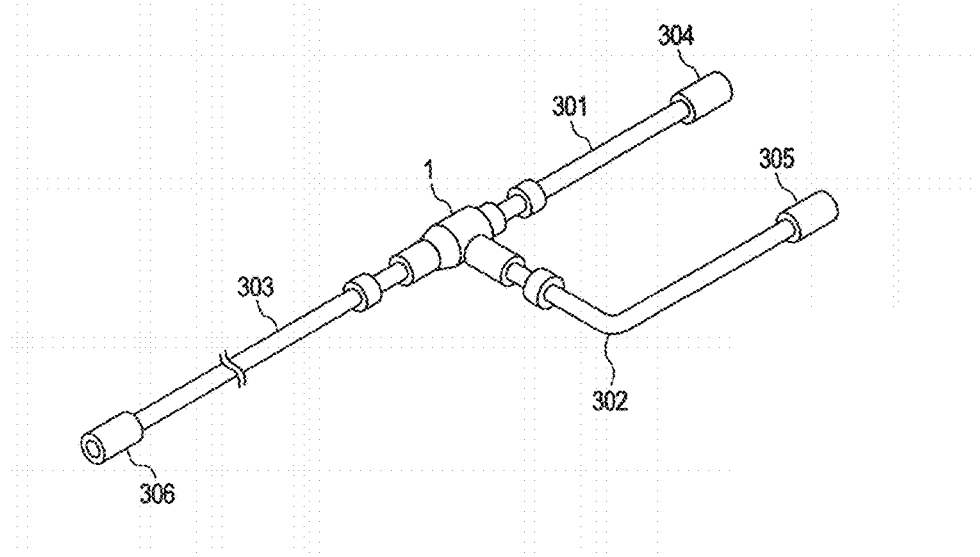

[Fig. 4]
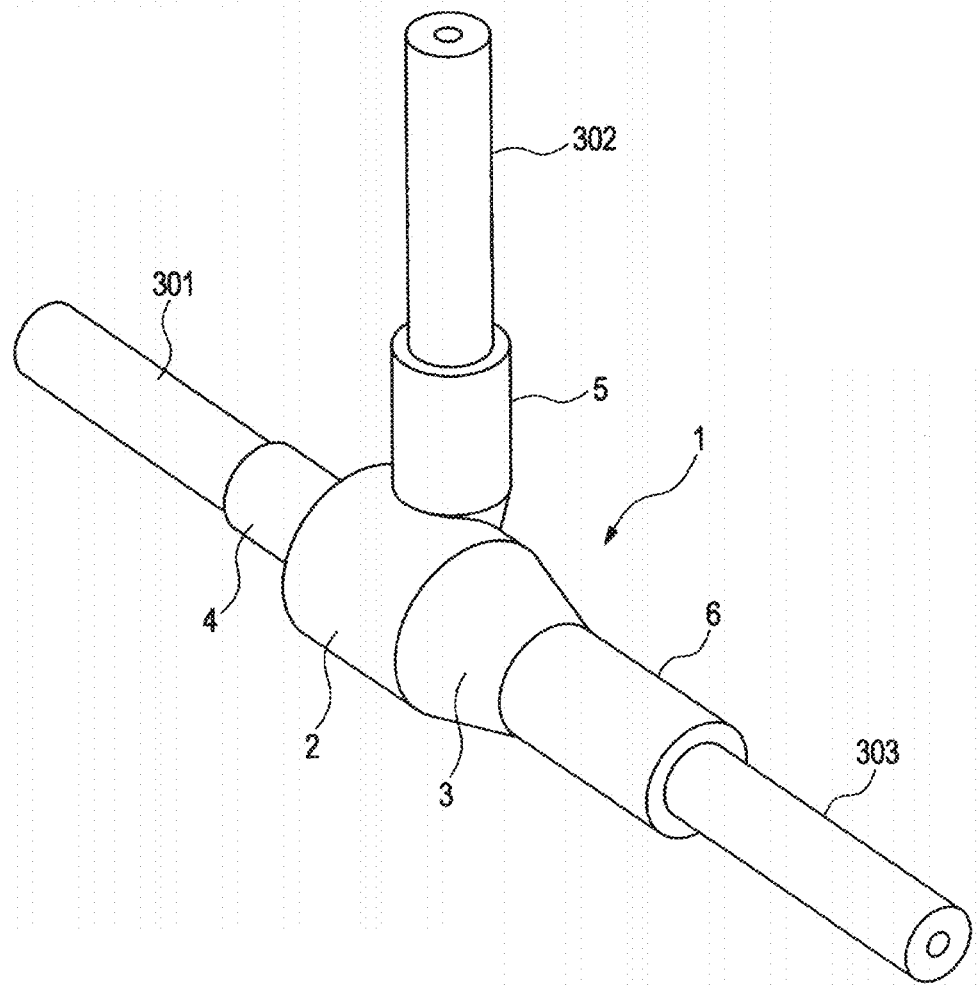

[Fig. 5]
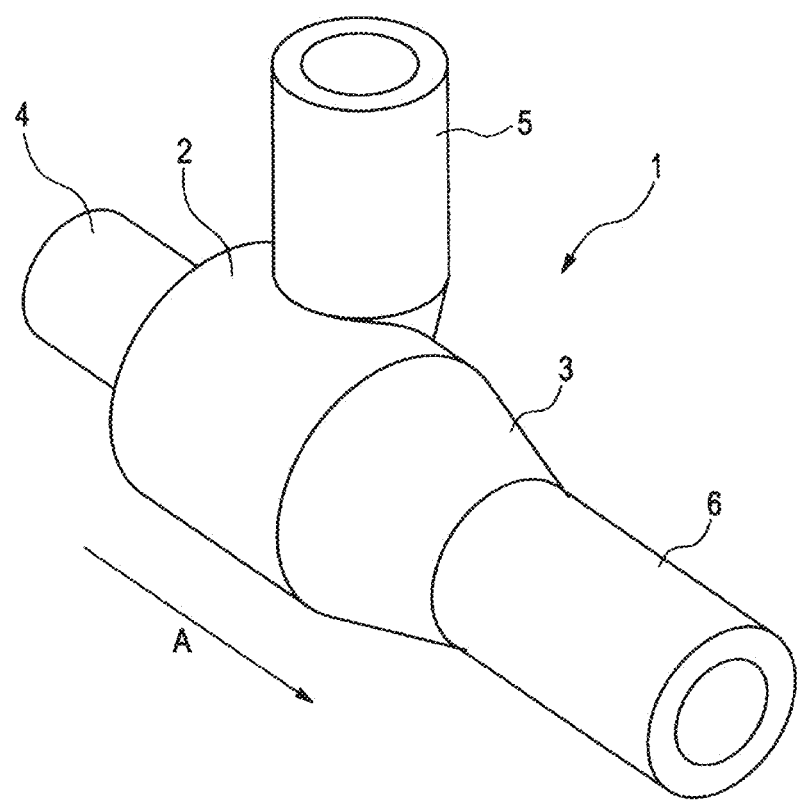
[Fig. 6]
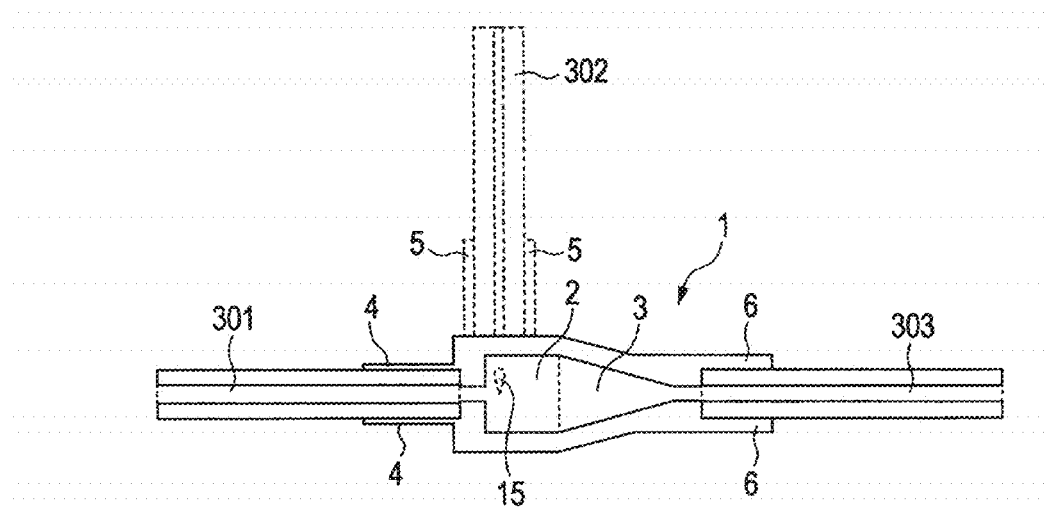

[Fig. 7]
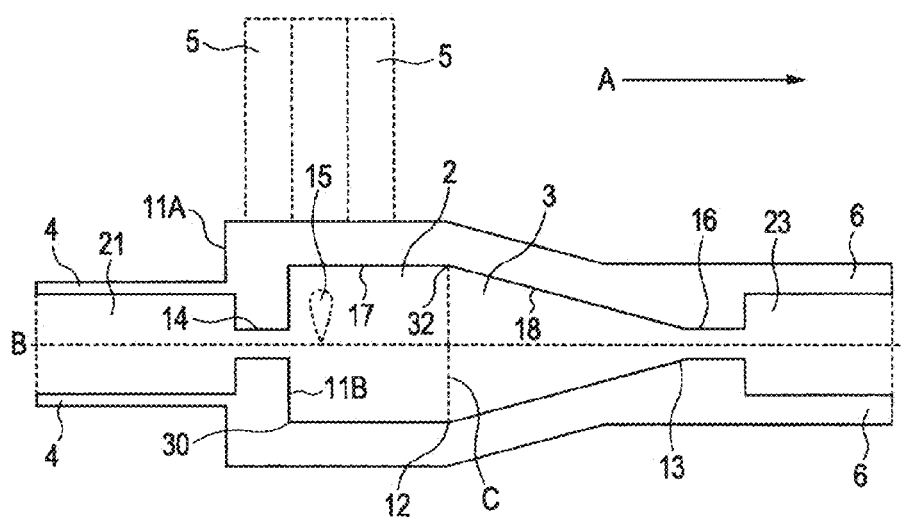

[Fig. 8]
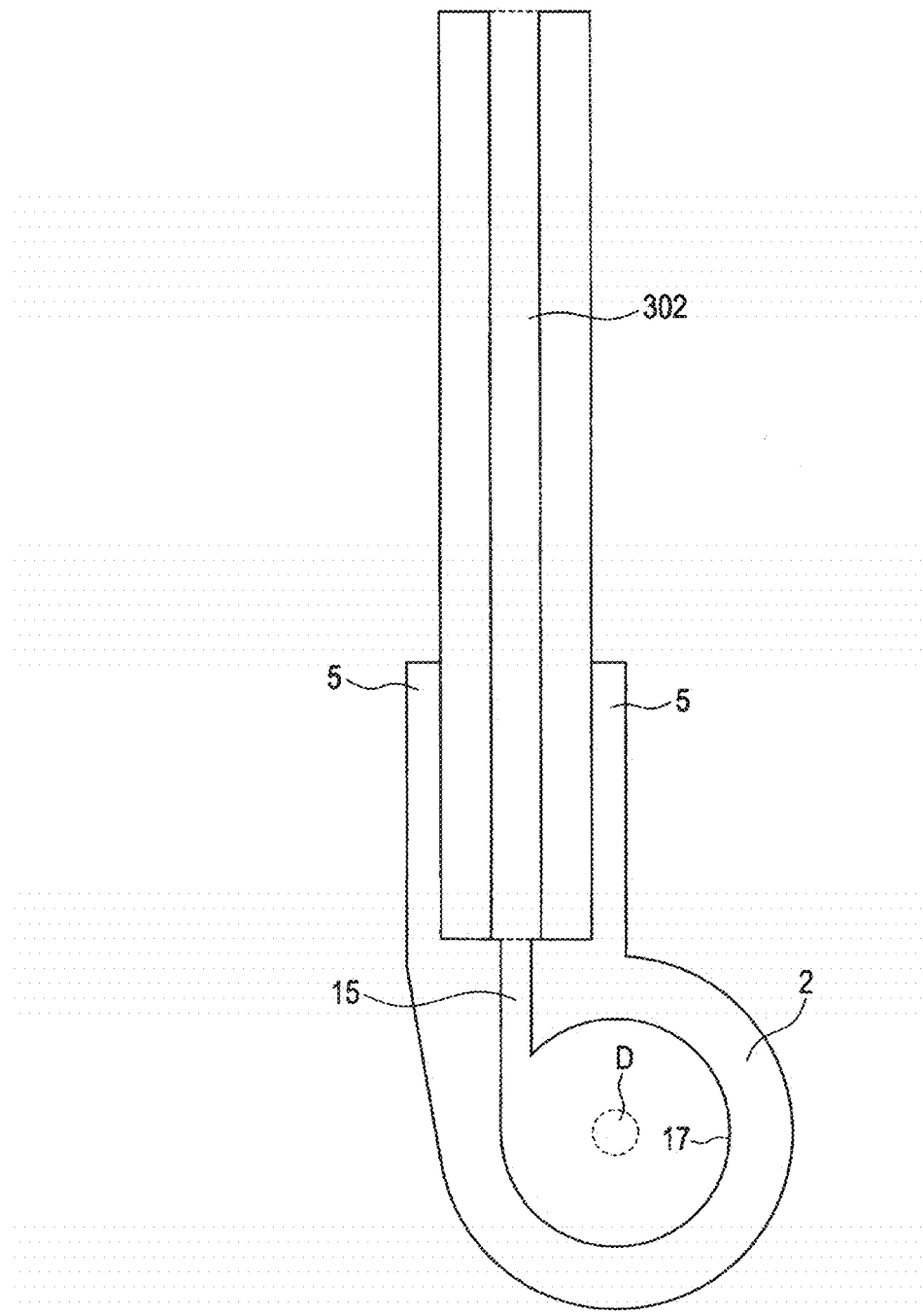

[Fig. 9]
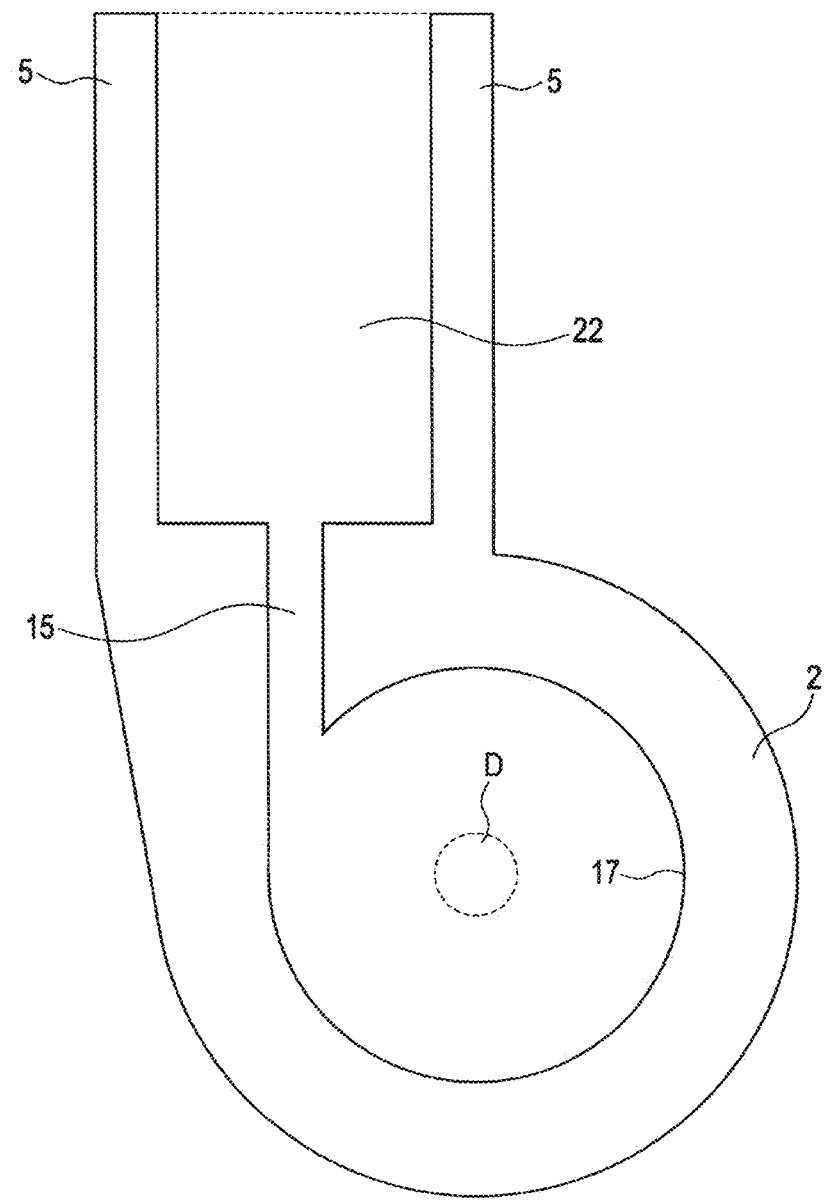

[Fig. 10]
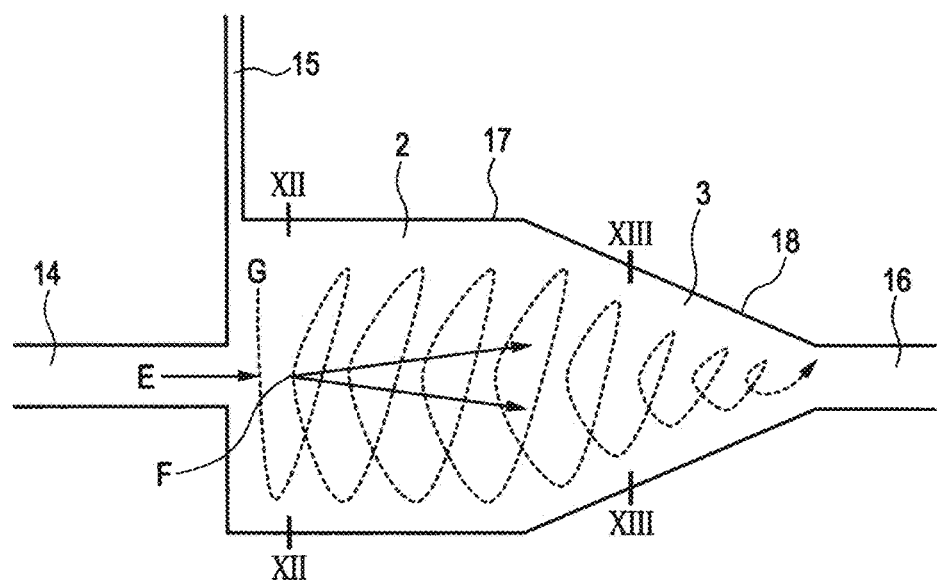
[Fig. 11]
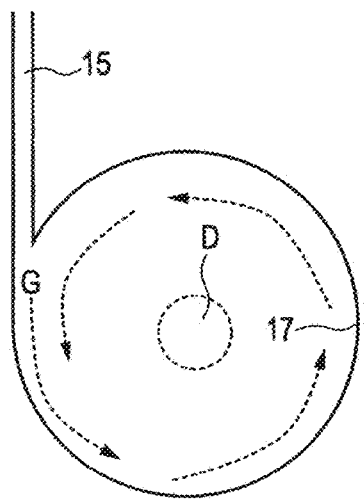

[Fig. 12]
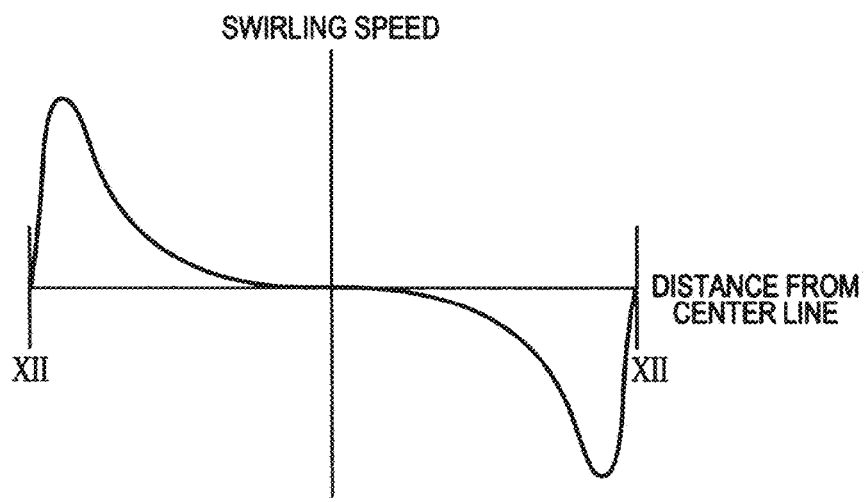
[Fig. 13]
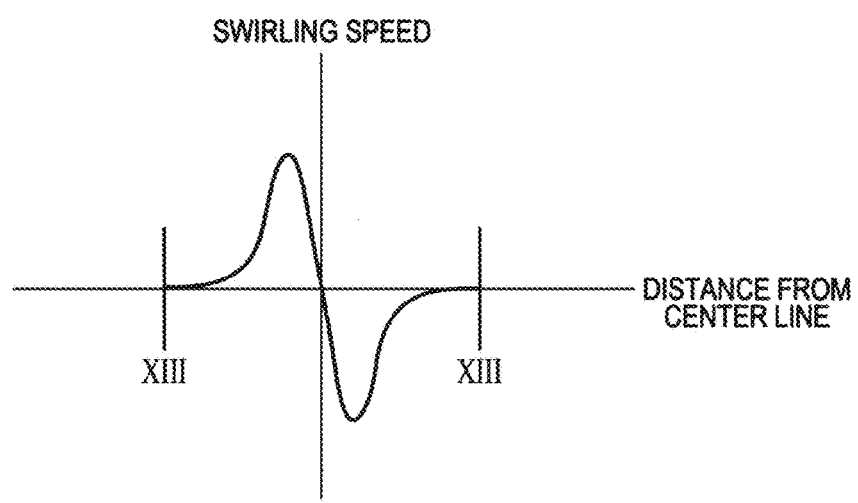

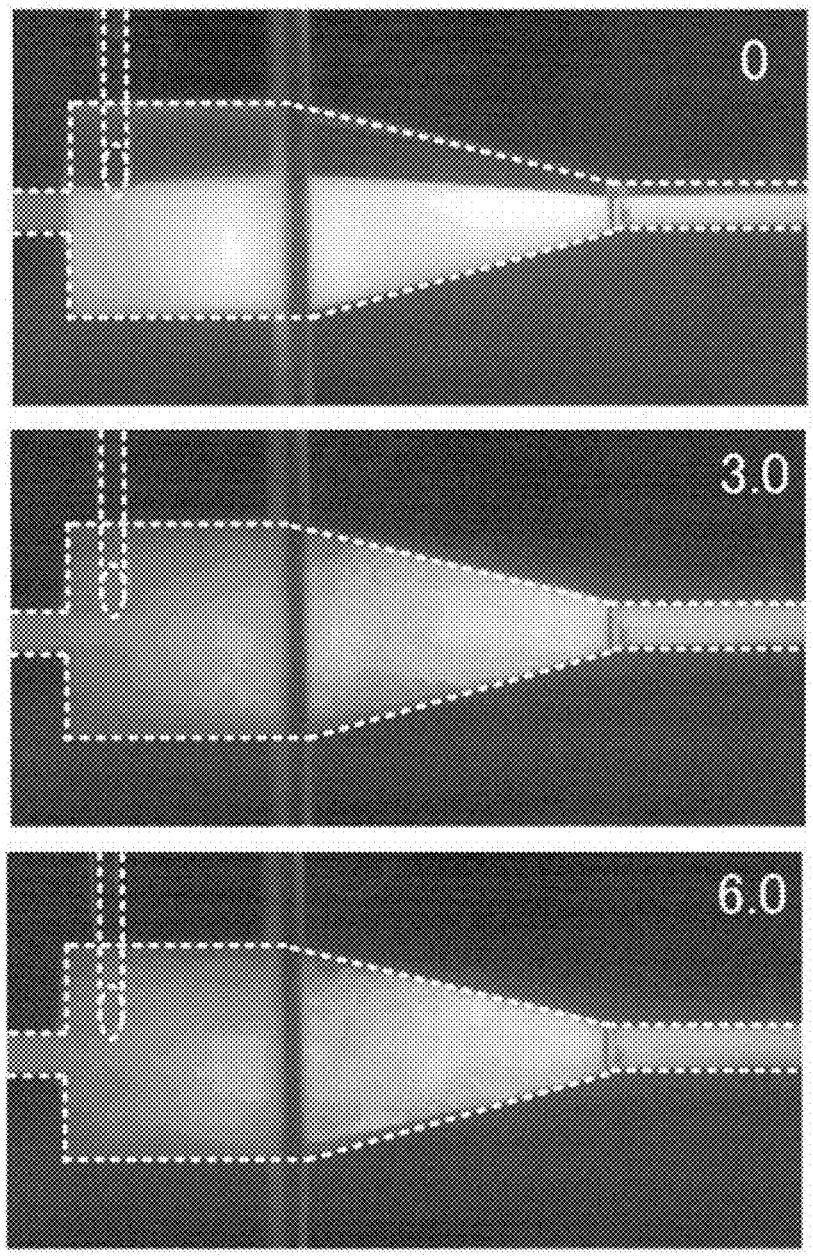
[Fig. 14]

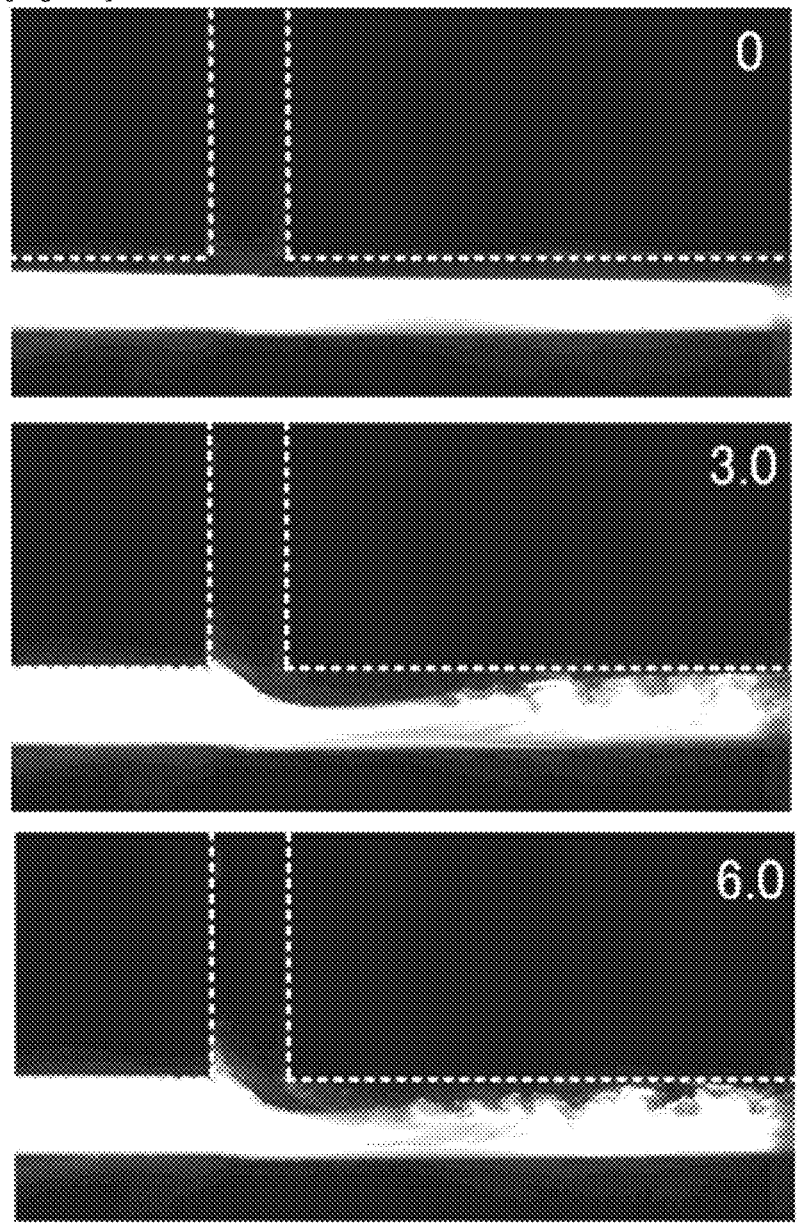
[Fig. 15]

[Fig. 16]
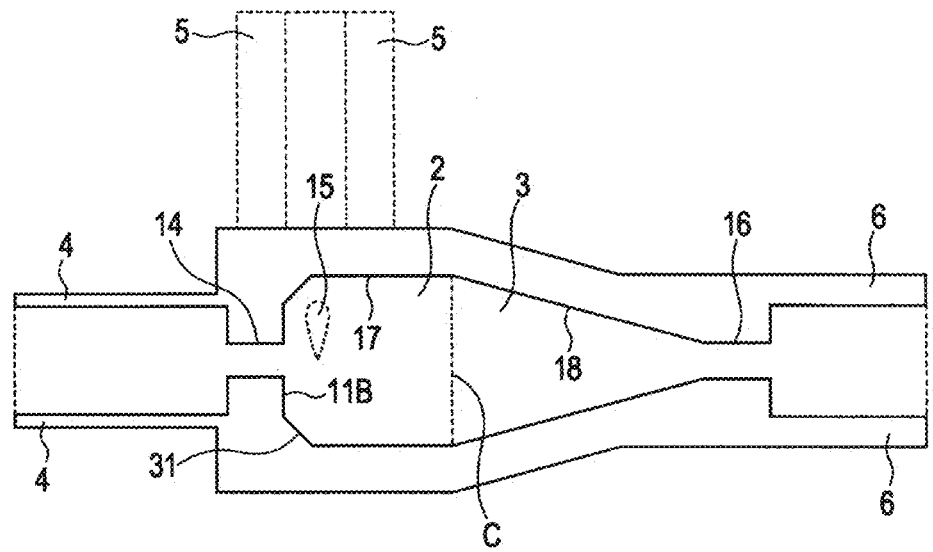
[Fig. 17]
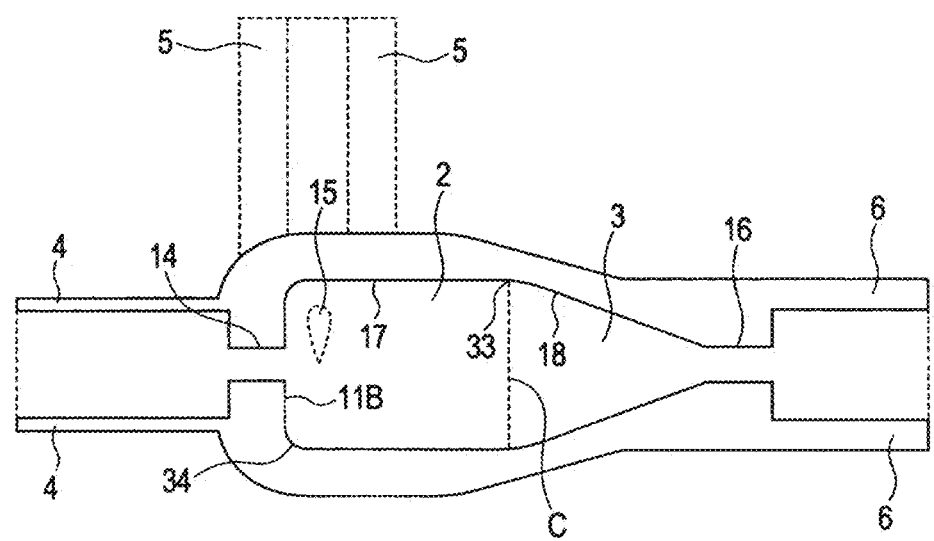

[Fig. 18]
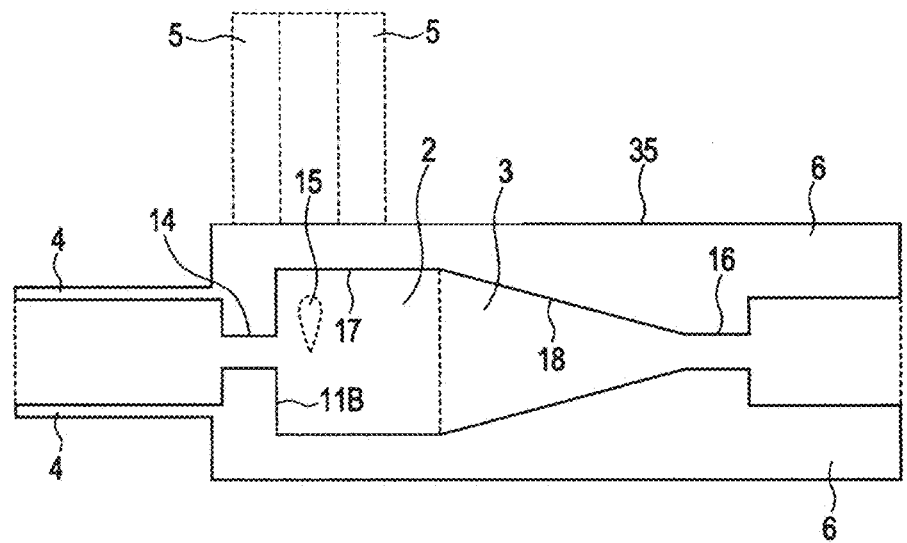
[Fig. 19]
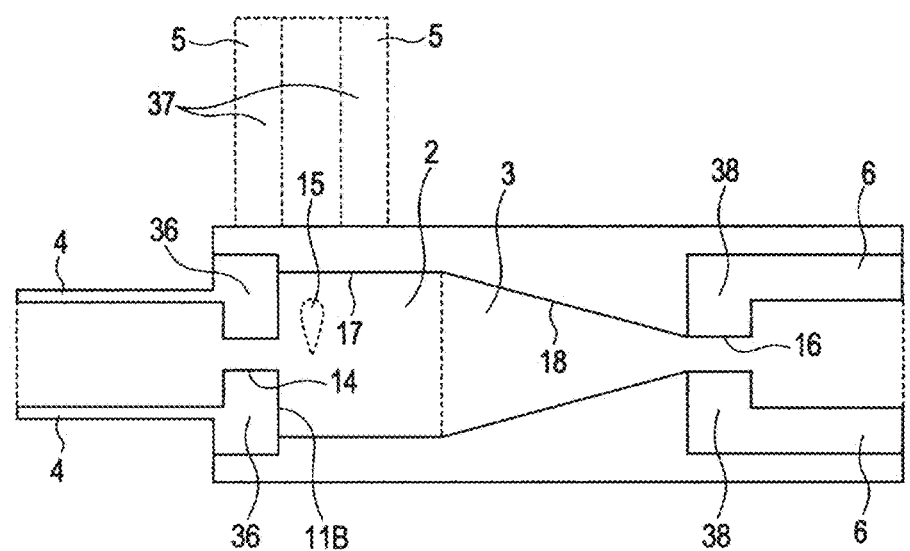

MIXING DEVICE, MIXING TUBE, DRUG SOLUTION INJECTING SYSTEM, AND DRUG SOLUTION MIXING METHOD

TECHNICAL FIELD

The present invention relates to a mixing device capable of mixing two kinds of drug solutions, a mixing tube having the mixing device, a drug solution injecting system having the mixing device and capable of injecting the mixed drug solutions, and a drug solution mixing method.

BACKGROUND ART

Currently, examples of a medical fluoroscopic imaging apparatus include a CT (Computed Tomography) scanner, an MRI (Magnetic Resonance Imaging) apparatus, a PET (Positron Emission Tomography) apparatus, an ultrasonic diagnostic apparatus, a CT angiography apparatus, an MR angiography apparatus, a vein imaging apparatus, and other apparatuses. When these apparatuses are used, for the purpose of obtaining clear images and the like, a plurality of kinds of drug solutions different in specific gravity or viscosity is injected into the body of a patient. For this purpose, for example, when contrast agent and saline are injected, a drug solution injecting apparatus having two syringes is used.

When the contrast agent and the saline are injected in this manner, a tube is connected to each of the two syringes, and the two tubes are connected via a T-shaped joint. Thus, the contrast agent and the saline are joined together in the joint portion and injected into the patient through an indwelling needle tapped into a blood vessel of the patient. For example, FIG. 2 in Patent Literature 1 discloses a T-shaped joint 45A.

CITATION LIST

Patent Literature

PTL 1: Japanese Patent Application Laid-Open No. 2009-247404

SUMMARY OF INVENTION

However, when the T-shaped joint is used, the contrast agent and the saline may not be mixed well before injection. More specifically, since the contrast agent and the saline are different in specific gravity and viscosity, the two kinds of drug solutions joined in the T-shaped joint may be separated into two layers, that is, a layer of the contrast agent having a high specific gravity and a layer of the saline having a low specific gravity.

As a result, in a surface where the layer of a drug solution having a high specific gravity contacts the layer of a drug solution having a low specific gravity, namely, in the two-dimensional surface, the two kinds of drug solutions are planarly mixed. However, the contrast agent having a high viscosity is unlikely to be mixed with the saline having a low viscosity, and thus, the contrast agent and the saline separated into the two layers may be injected as is. Note that in the following description, the above-mentioned planarly mixing is referred to as a two-dimensional mixing.

When small amounts of contrast agent and saline are injected, the injection time is short, and thus, it takes a short time to join and mix the contrast agent and the saline. Therefore, sufficient mixing may not be achieved. When the drug solutions are injected in a state of being separated into the two layers, the concentration of the injected contrast agent may be different depending on the place. As a result, unevenness may occur in an image taken by a fluoroscopic imaging apparatus. Such image unevenness may make it hard to determine the lesioned area, and may make it hard to image the blood vessel clearly.

In order to solve this problem, there may be a method of mixing the contrast agent and the saline in advance. However, the amount of the contrast agent to be injected is different for each patient. Therefore, the method of mixing the contrast agent and the saline in advance requires performing the operation of mixing the contrast agent and the saline independently for each imaging. Moreover, when the contrast agent and the saline are mixed, the mixed drug solutions may be contaminated.

In order to solve the above problems, the mixing device according to the present invention includes: a swirling flow generating chamber adapted for generating a swirling flow; a first inflow opening adapted for introducing a first drug solution into the swirling flow generating chamber in a direction parallel to a central axis of the swirling flow; a second inflow opening adapted for introducing a second drug solution into the swirling flow generating chamber so as to generate a swirling flow of the second drug solution having a specific gravity lower than that of the first drug solution in the swirling flow generating chamber; an outflow opening adapted for discharging a mixed drug solution of the first drug solution and the second drug solution; and a narrowing chamber which is interposed between the swirling flow generating chamber and the outflow opening and has a space continuously narrowed toward the outflow opening.

Further, the mixing tube according to the present invention includes: a first tube communicated with the first inflow opening; a second tube communicated with the second inflow opening; a third tube communicated with the outflow opening; and the mixing device.

Further, the drug solution injecting system according to the present invention includes: a drug solution injecting apparatus having a head to which a first syringe filled with the first drug solution and a second syringe filled with the second drug solution are attached, and a controller connected to the head; and the mixing tube connected to the first syringe and the second syringe.

Further, the drug solution mixing method according to the present invention comprises: generating a swirling flow of a second drug solution; introducing a first drug solution in a direction parallel to a central axis of the swirling flow; guiding the first drug solution and the second drug solution into a space continuously narrowed toward an outflow opening to collide the first drug solution and the second drug solution; and discharging a mixed drug solution of the first drug solution and the second drug solution from the outflow opening.

According to the present invention, a plurality of kinds of drug solutions can be mixed evenly and efficiently at a desired concentration when injected without a need to perform a mixing operation separately as an independent operation. Further, even small amounts of drug solutions can be mixed at a high mixing efficiency. Thus, the present invention can exert effects of preventing unevenness from occurring in an image taken by a fluoroscopic imaging apparatus.

BRIEF DESCRIPTION OF DRAWINGS

FIG. 1 is a perspective view of a drug solution injecting system.

FIG. 2 is a perspective view of a head to which mixing tube is connected.

FIG. 3 is a perspective view of the mixing tube.

FIG. 4 is a perspective view of a mixing device to which tubes are connected.

FIG. 5 is perspective view of the mixing device.

FIG. 6 is a schematic longitudinal cross-sectional view of the mixing device to which the tubes are connected.

FIG. 7 is a schematic longitudinal cross-sectional view of the mixing device.

FIG. 8 is a schematic lateral cross-sectional view of the mixing device to which the tubes are connected.

FIG. 9 is a schematic lateral cross-sectional view of the mixing device.

FIG. 10 is a schematic longitudinal view inside the mixing device.

FIG. 11 is a schematic lateral view inside the mixing device.

FIG. 12 illustrates a swirling speed profile of a vortex in a cross section along line XII-XII of FIG. 10.

FIG. 13 illustrates a swirling speed profile of a vortex in a cross section along line XIII-XIII of FIG. 10.

FIG. 14 is a series of images obtained by imaging the mixed state using the mixing device.

FIG. 15 is a series of images obtained by imaging the mixed state using a T-shaped joint.

FIG. 16 is a schematic longitudinal cross-sectional view of the mixing device in a first embodiment.

FIG. 17 is a schematic longitudinal cross-sectional view of the mixing device in a second embodiment.

FIG. 18 is a schematic longitudinal cross-sectional view of the mixing device in a third embodiment.

FIG. 19 is a schematic longitudinal cross-sectional view of the mixing device in a fourth embodiment.

DESCRIPTION OF EMBODIMENTS

FIG. 1 is a perspective view of a drug solution injecting system 100 having a mixing device 1 in the present invention. The drug solution injecting system 100 includes a drug solution injecting apparatus 200 (injector) for injecting a drug solution such as a contrast agent into a patient, a first syringe 201 and a second syringe 202 attached to the drug solution injecting apparatus 200, and a mixing tube 300 connected to the first syringe 201 and the second syringe 202. Further, a fluoroscopic imaging apparatus (not shown) is connected to a main unit 212 of the drug solution injecting system 100. When a drug solution is injected and when an image is taken, various kinds of data are sent and received between the fluoroscopic imaging apparatus and the drug solution injecting system 100.

The drug solution injecting apparatus 200 includes a head 210 to which the first syringe 201 and the second syringe 202 are attached, and a main unit 212 connected to the head 210 through a head cable 211. The main unit 212 is connected to a power source (not shown) through a power cable 218. Note that in FIG. 1, the first syringe 201 and the second syringe 202 are housed in protective syringe case. The conduit pipe portion at the front end of the first syringe 201 and the second syringe 202 is exposed from the protective syringe case.

The first syringe 201 is filled with a drug solution having a high specific gravity and the second syringe 202 is filled with a drug solution having a low specific gravity. In the present example, the first syringe 201 is filled with a contrast agent, and the second syringe 202 is filled with saline. The first syringe 201 and the second syringe 202 may be a pre-filled-type syringe which has been filled with a drug solution in advance or a suction-type syringe which sucks a drug solution from a drug solution bag.

Specific examples of the contrast agent include a contrast agent having an iodine concentration of 240 mg/ml (e.g., having a viscosity of 3.3 pascal second and a specific gravity of 1.268 to 1.296 at 37 degrees Celsius), a contrast agent having an iodine concentration of 300 mg/ml (e.g., having a viscosity of 6.1 milli pascal second and a specific gravity of 1.335 to 1.371 at 37 degrees Celsius), and a contrast agent having an iodine concentration of 350 mg/ml (e.g., having a viscosity of 10.6 milli pascal second and a specific gravity of 1.392 to 1.433 at 37 degrees Celsius). Further, specific examples of saline include saline containing 180 mg of sodium chloride of in 20 mL of saline (e.g., having a viscosity of 0.9595 milli pascal second and a specific gravity of 1.004 to 1.006 at 20 degrees Celsius).

The head 210 is rotatably held on an upper portion of a stand pole 217 on a mobile stand base 216 placed on a floor surface. Thus, the head 210 can be rotated to a position in which the front end side (the side to which the first syringe 201 and the second syringe 202 are attached) of the head 210 faces the floor surface and a position in which the rear end side (the side to which the first syringe 201 and the second syringe 202 are not attached) of the head 210 faces the floor surface.

A console 213 has a touch panel and is connected to a hand switch 214 through a cable. The console 213 functions as a controller. The console 213 is connected to the main unit 212 through a console cable 215 and is connected to the head 210 through the main unit 212 and the cables 215 and 211. The main unit 212 is connected to the head 210 through the head cable 211. When a drug solution is injected to a patient, the operator operates the touch panel to enter the injection speed, the injection amount, the injection time, physical data of the patient such as body weight, data about the kind of the drug solution, and the like.

Data about an operation pattern (injection protocol), data about the drug solutions, and other data are preliminarily stored in the console 213. The console 213 calculates an optimal injection condition according to the entered data and the pre-stored data. Then, the console 213 determines the amount of the drug solution to be injected into the patient and the injection protocol based on the calculated injection condition.

When the amount of the drug solution and the injection protocol are determined, the console 213 displays predetermined data or a graph or the like on the touch panel. The operator confirms the displayed data or a graph or the like, and then presses a decision button on the touch panel to actually start the injection operation. When the decision button is pressed, the console 213 instructs the head 210 to start injecting the drug solution. The injection also starts by pressing the button of the hand switch 214. While the button of the hand switch 214 is being pressed, the injection continues.

FIG. 2 is a perspective view of the head 210 of the drug solution injecting apparatus 200 and the mixing tube 300 of the drug solution injecting system 100. Each front end of the first syringe 201 and the second syringe 202 attached to the head 210 has a conduit pipe portion. The mixing tube 300 having the mixing device 1 of the present invention is connected to the conduit pipe portion. Further, the mixing tube 300 is communicated with a catheter 103 through a flexible tube 105, a branch pipe (not shown), a catheter hub 104, and the like. In FIG. 2, the first syringe 201 and the second syringe 202 are housed inside the protective syringe case.

The conduit pipe portions at the front end of the first syringe 201 and the second syringe 202 are exposed from the protective syringe case. The conduit pipe portion of the first syringe 201 is connected to the first tube 301 of the mixing tube 300. Further, the conduit pipe portion of the second syringe 202 is connected to the second tube 302 of the mixing tube 300.

Further, a plunger (not shown) is attached to the first syringe 201 and the second syringe 202. The first syringe 201 and the second syringe 202 are fixed to the protective syringe case with the respective plungers attached thereto. The protective syringe case is fixed to the head 210 by a syringe clamper.

Further, the head 210 includes two syringe pressers (not shown). Each syringe presser engages with an engaging portion of the plunger attached to the first syringe 201 and the second syringe 202 to operate so as to press the plunger in and out. When a drug solution is sucked, suction tubes for filling are attached to the conduit pipe portions at the front end of the first syringe 201 and the second syringe 202 to supply the drug solution from drug solution bags through the suction tubes. At this time, the syringe presser moves the plunger forward to the front end portion of the syringe and then moves the plunger backward to the rear end portion of the syringe along the axial direction of the first syringe 201 and the second syringe 202.

When the drug solution is injected, the mixing tube 300 is attached to the conduit pipe portions at the front ends of the first syringe 201 and the second syringe 202. Then, the syringe presser advances the plunger in the axial direction of the first syringe 201 and the second syringe 202. This causes the contrast agent to be pressed out from the first syringe 201 and the saline to be pressed out from the second syringe 202. Each of the two syringe pressers may be driven separately or may be driven simultaneously.

The pressed out contrast agent and saline are flowed into the mixing device 1 of the mixing tube 300 and are mixed in the mixing device 1. Then, the mixed drug solution of the contrast agent and the saline is injected into a blood vessel of the patient through the catheter 103.

Before the drug solution is injected, priming is performed for the purpose of bleeding air. There are several priming methods. The mixing tube 300 is filled with one of the drug solutions of the saline and the contrast agent. Specifically, first, the contrast agent is pressed out of the first syringe 201 to fill the first tube 301 up to the mixing device 1 with the contrast agent. Next, saline is pressed out of the second syringe 202 to fill the second tube 302, the mixing device 1, the third tube 303, and the line from the third tube 303 to the catheter 103 with the saline. As a result, the mixing tube 300 and the entire drug solution line from the mixing tube 300 to the catheter 103 are filled with the drug solution with air bleeded.

In addition, there is another method. First, the contrast agent is pressed out of the first syringe 201, and then, the saline is pressed out of the second syringe 202. Then, the drug solutions are pressed out of the first syringe 201 and the second syringe 202 at the same time. Further, there is another method. First, the saline is pressed out of the second syringe 202, and then, the contrast agent is pressed out of the first syringe 201 to fill the entire drug solution line with the drug solutions.

In addition to the above methods, there is another method. First, the saline is pressed out of the second syringe 202, and then, the contrast agent is pressed out of the first syringe 201. Then, the drug solutions are pressed out of the first syringe 201 and the second syringe 202 at the same time. Furthermore, from the start, the drug solutions are pressed out of the first syringe 201 and the second syringe 202 at the same time to fill the entire drug solution line with the drug solutions.

FIG. 3 is a perspective view of the mixing tube 300 having the mixing device 1 in the present invention. The mixing tube 300 includes, a first tube 301 connecting the first syringe 201 and the mixing device 1, a second tube 302 connecting the second syringe 202 and the mixing device 1, and a third tube 303 connecting the flexible tube 105 and the mixing device 1. A drug solution having a high specific gravity passes through the first tube 301, a drug solution having a low specific gravity passes through the second tube 302, and the mixed drug solution passes through the third tube 303. In the present example, the first tube 301, the second tube 302, and the third tube 303 are a flexible tube. However, these tubes may be a rigid tube.

The first tube 301 has a first connection portion 304 connected to the conduit pipe portion at the front end of the first syringe 201. The second tube 302 has a second connection portion 305 connected to the conduit pipe portion at the front end of the second syringe 202. The third tube 303 has a third connection portion 306 connected to the flexible tube 105. The first connection portion 304, the second connection portion 305, and the third connection portion 306 are connected by threaded connection, bonding, or the like.

Further, a unidirectional valve may be provided on the first tube 301 or the second tube 302. The unidirectional valve can prevent the mixed drug solution and the like from flowing back to the first syringe 201 side or the second syringe 202 side.

FIGS. 4 and 5 are a perspective view of the mixing device 1 in the present invention. FIG. 4 illustrates the mixing device 1 to which the first tube 301, the second tube 302, and the third tube 303 are connected. FIG. 5 illustrates the mixing device 1 to which these tubes are not connected.

The mixing device 1 in the present example includes a first chamber which is a swirling flow generating chamber 2 for generating a swirling flow, and a second chamber which is a narrowing chamber 3 for concentrating the swirling flow in an axial direction. The swirling flow generating chamber 2 in the present example has a cylindrical outer shape and a columnar inner space. The narrowing chamber 3 in the present example has a funnel outer shape and a conical internal space coaxial with the internal space of the swirling flow generating chamber 2.

The lateral cross-sectional shape of the swirling flow generating chamber 2 may be a circle, an ellipse, and other various shapes made of curved lines. For example, the swirling flow generating chamber 2 may be formed into a narrow shape such that the closer to the narrowing chamber 3, the front of the swirling flow generating chamber 2 is narrowed. In this case, the inner surface of the swirling flow generating chamber 2 and the inner surface of the narrowing chamber 3 are formed into one surface inclined at the same inclination with respect to the central axis line of the conical space of the swirling flow generating chamber 2. Further, the narrow shape of the swirling flow generating chamber 2 may be configured in such a manner that the inclination of the inner surface of the narrowing chamber 3 with respect to the central axis line of the swirling flow generating chamber 2 is greater than the inclination of the inner surface of swirling flow generating chamber 2 with respect to the central axis line of the swirling flow generating chamber 2.

In FIG. 5, the flow direction A of the mixed drug solution is indicated by an arrow. At an upstream position from the center of the swirling flow generating chamber 2 in the flow direction A, there is provided a cylindrical first conduit pipe portion 4 connected to the first tube 301 so as to extend along the flow direction A. Likewise, at an upstream position from the center of the swirling flow generating chamber 2 in the flow direction A, there is provided a cylindrical second conduit pipe portion 5 connected to the second tube 302. Further, at a downstream position from the center of the narrowing chamber 3 in the flow direction A, there is provided a cylindrical third conduit pipe portion 6 connected to the third tube 303.

The first conduit pipe portion 4 to which a drug solution having a high specific gravity is supplied is communicated with the first inflow opening 14 (FIG. 7) of the swirling flow generating chamber 2. Therefore, the first conduit pipe portion 4 is provided on the upstream side in the flow direction A and at the center of the outside end surface 11A in front of the swirling flow generating chamber 2. In addition, the third conduit pipe portion 6 from which the mixed drug solution is discharged is provided at an end portion of the outflow opening 16 in such a manner that the center line of the third conduit pipe portion 6 matches the center line of the first conduit pipe portion 4, namely, both the conduit pipe portions are coaxial with each other.

Meanwhile, the second conduit pipe portion 5 to which a drug solution having a low specific gravity is supplied is communicated with the second inflow opening 15 of the swirling flow generating chamber 2. Therefore, the second conduit pipe portion 5 is provided on a curved side surface outside the swirling flow generating chamber 2 and extends in the tangential direction of the circumference of the swirling flow generating chamber 2 with a circular cross section. More specifically, the second conduit pipe portion 5 in the present example is provided at a position shifted to a peripheral side of the swirling flow generating chamber 2 from the central axis line of the columnar space of the swirling flow generating chamber 2. Thereby, a swirling flow of the drug solution having a low specific gravity supplied from the second conduit pipe portion 5 is generated.

In the present example, the contrast agent is supplied from the first conduit pipe portion 4 and the saline is supplied from the second conduit pipe portion 5. Then, the contrast agent and the saline are mixed in the swirling flow generating chamber 2 and the narrowing chamber 3. Then, the mixed drug solution of the contrast agent and the saline is discharged from the third conduit pipe portion 6.

The swirling flow generating chamber 2 may be of any size allowing an appropriate volume to be formed in a space from the second conduit pipe portion 5 to the narrowing chamber 3 as long as a vortex is generated therein. Therefore, if the space from the second conduit pipe portion 5 to the narrowing chamber 3 has a sufficient volume, the second conduit pipe portion 5 may be provided near the center of the swirling flow generating chamber 2. Even in this case, the second conduit pipe portion 5 is provided on a side surface of the swirling flow generating chamber 2 and extends in the tangential direction of the circumference of the swirling flow generating chamber 2.

FIGS. 6 and 7 are a schematic longitudinal cross-sectional view of the mixing device 1 in the present invention. Specifically, FIGS. 6 and 7 are a schematic lengthwise cross-sectional view along the center line of the first conduit pipe portion 4, the swirling flow generating chamber 2, the narrowing chamber 3, and the third conduit pipe portion 6. Note that the portion not appearing in the cross section along the center line is indicated by dotted lines for descriptive purposes. FIG. 6 illustrates the mixing device 1 to which the first tube 301, the second tube 302, and the third tube 303 are connected, while FIG. 7 illustrates the mixing device 1 to which these tubes are not connected.

The swirling flow generating chamber 2 has a curved inner surface 17 which is a circumferential inner surface forming a columnar space. The second inflow opening 15 extends in the tangential direction of the circumference of the curved inner surface 17. This causes a drug solution supplied from the second inflow opening 15 to generate a swirling flow. The narrowing chamber 3 is interposed between the swirling flow generating chamber 2 and the outflow opening 16 and has a narrow shape continuously narrowed toward the outflow opening 16. Further, the narrowing chamber 3 has an inner surface 18 inclined toward the outflow opening 16 and is communicated with the swirling flow generating chamber 2 so as to form a funnel-shaped space. As a result, the generated swirling flow is concentrated in the central axis direction of the vortex.

The first conduit pipe portion 4 to which a contrast agent is supplied is communicated with the swirling flow generating chamber 2 through the first inflow opening 14. This allows the drug solution having a high specific gravity passing through the first inflow opening to be introduced into the swirling flow generating chamber 2 in a direction parallel to the central axis of the swirling flow of the drug solution having a low specific gravity. In other word, the drug solution having a high specific gravity is introduced in a direction parallel to the central axis line of the columnar space of the swirling flow generating chamber 2. The second conduit pipe portion 5 to which saline is supplied is communicated with the swirling flow generating chamber 2 through the second inflow opening 15. This allows the saline to be introduced in the swirling flow generating chamber 2 so as to cause a swirling flow to be generated in the swirling flow generating chamber 2.

The second conduit pipe portion 5 extends in a direction crossing the central axis line of the swirling flow generating chamber 2. Further, the swirling flow generating chamber 2 is communicated with a large-diameter side opening 12 of the narrowing chamber 3 at a boundary C indicated by dotted lines in the figure. The narrowing chamber 3 is communicated with the outflow opening 16 through a small-diameter side opening 13. In the present example, the second conduit pipe portion 5 extends in a direction orthogonal to the central axis line of the swirling flow generating chamber 2, but the second conduit pipe portion 5 may extend in a direction inclined to the central axis line of the swirling flow generating chamber 2.

In the present example, the center line of the first inflow opening 14, the central axis line of the swirling flow generating chamber 2, the central axis line of the narrowing chamber 3, and the center line of the outflow opening 16 are overlapped with a straight line B (center line of the mixing device 1) indicated by dotted lines in the figure. For as much as the components are coaxially-arranged, the isotropy of vortex generated in the mixing device 1 is increased. Thus, vortex can be generated smoothly and evenly in the space, thereby increasing the mixing efficiency.

The first tube 301 is bonded into a first receiving portion 21 formed inside the first conduit pipe portion 4. The third tube 303 is bonded into a third receiving portion 23 formed inside the third conduit pipe portion 6. Note that the first tube 301 and the third tube 303 may be threadedly connected to the first receiving portion 21 and the third receiving portion 23 respectively.

In a case where the drug solution having a low specific gravity has a low flow rate, its flow may collide with the drug solution having a high specific gravity remaining stagnant in the mixing device 1 when the injection starts, which may attenuate the inertial force of the swirling flow. When the inertial force is attenuated, the swirling strength becomes insufficient and the vortex cannot be generated at short time. Alternatively, it takes time to grow the generated vortex until the flow rate of the vortex becomes sufficiently high. Therefore, the mixing efficiency of the drug solutions is reduced.

In light of this, in the present example, the inner diameter of the second inflow opening 15 indicated by dotted lines in the figure is set to be narrower than the inner diameter of the first inflow opening 14. In short, the second inflow opening 15 through which the drug solution having a low specific gravity is supplied is narrower than the first inflow opening 14 through which the drug solution having a high specific gravity is supplied. More specifically, the inner diameter of the second inflow opening 15 is formed approximately two-thirds to one-third of the inner diameter of the first inflow opening 14. For example, when the inner diameter of the first inflow opening 14 is 1.5 mm, the inner diameter of the second inflow opening 15 is 1 mm to 0.5 mm.

Thus, when the drug solutions are injected at a predetermined pressure, the flow rate of the drug solution having a low specific gravity supplied from the second inflow opening 15 with a small cross section area is higher than the flow rate of the drug solution having a high specific gravity supplied from the first inflow opening 14 with a large cross section area. Note that the present invention is not limited to the configuration in which the flow rate of the drug solution having a low specific gravity is higher than the flow rate of the drug solution having a high specific gravity, but may be applied to the configuration in which both the flow rates are the same. In this case, for example, the inner diameter of the second inflow opening 15 is the same as the inner diameter of the first inflow opening 14.

In the present example, the inner diameter of the swirling flow generating chamber 2 and the inner diameter of the large-diameter side opening 12 of the narrowing chamber 3 are 7.5 mm, and the inner diameter of the small-diameter side opening 13 of the narrowing chamber 3 and the inner diameter of the outflow opening 16 are 1.5 mm. In addition, the inclined inner surface 18 of the narrowing chamber 3 is inclined at 15 degrees with respect to the central axis line of the narrowing chamber 3. Further, in the flow direction A parallel to the central axis line of the swirling flow generating chamber 2 indicated by an arrow in FIG. 7, the length of the swirling flow generating chamber 2 is 7.5 mm and the length of the narrowing chamber 3 is 11.2 mm.

Note that these sizes are just an example thereof, and the size of the mixing device 1 in the present invention is not limited to these. For example, the inclined inner surface 18 of the narrowing chamber 3 may be configured such that the closer to the outflow opening 16, the narrower the inner space of the narrowing chamber 3 becomes in an axisymmetric form. The angle at the boundary C between the swirling flow generating chamber 2 and the narrowing chamber 3 can change smoothly. This is because resistance force will occur in a portion with a large change in angle, namely, a corner.

Hydrophilic processing may be performed on the inner surface of the mixing device 1 in the present invention. The hydrophilic processing can prevent air bubbles from attaching to the inner surface of the mixing device 1 at air bleeding. Examples of the hydrophilic processing method include plasma processing, ozone processing, corona discharge processing, glow discharge processing, ultraviolet irradiation processing, and the like. The hydrophilic processing may be performed at least one surface of the curved inner surface 17 of the swirling flow generating chamber 2, the inside end surface 11B in front of the swirling flow generating chamber 2, and the inclined inner surface 18 of the narrowing chamber 3.

FIGS. 8 and 9 are a schematic lateral cross-sectional view of the mixing device 1 in the present invention. More specifically, FIGS. 8 and 9 are a schematic cross-sectional view along the center line of the second conduit pipe portion 5, namely, a schematic cross-sectional view in a direction orthogonal to the central axis line D of the swirling flow generating chamber 2 schematically indicated by dotted lines in the figure. The portion not appearing in the cross section along the center line of the second conduit pipe portion 5 is indicated by dotted lines for descriptive purposes. FIG. 8 illustrates the mixing device 1 to which the second tube 302 is connected, while FIG. 9 illustrates the mixing device 1 to which the second tube 302 is not connected.

The second tube 302 to which saline is applied is bonded into the second receiving portion 22 formed inside the second conduit pipe portion 5. The second conduit pipe portion 5 extends in the tangential direction of the circumference of the swirling flow generating chamber 2. The second conduit pipe portion 5 is arranged to continue from the curved side surface outside the swirling flow generating chamber 2. Therefore, the second inflow opening 15 opens in a curved shape along the shape of the curved inner surface 17 of the swirling flow generating chamber 2. Note that the second tube 302 may be threadedly connected to the second receiving portion 22.

By referring to FIGS. 10 and 11, the description will focus on the mixing using a swirling flow generated in the mixing device 1 in the present invention. In the following description, the mixing process using a swirling flow generated in the mixing device 1 is referred to as a spiral flow. In FIGS. 10 and 11, a solid arrow indicates the flow of a contrast agent which is a drug solution having a high specific gravity, and a dotted arrow indicates the flow of saline which is a drug solution having a low specific gravity. The dotted circle D in FIG. 11 schematically indicates the position of the central axis line of the swirling flow generating chamber 2.

The contrast agent supplied from the first syringe 201 through the first tube 301 passes through the first inflow opening 14 with a small inner diameter into the swirling flow generating chamber 2 as a jet stream indicated by an arrow E. The momentum of the jet stream is diffused in an outer circumferential direction of the swirling flow generating chamber 2 as indicated by an arrow F. In short, the contrast agent flow is diffused in an outer circumferential direction of the swirling flow generating chamber 2.

The saline supplied from the second syringe 202 through the second tube 302 is guided through the second inflow opening 15 to the curved inner surface 17 of the swirling flow generating chamber 2, and is swirled along the curved inner surface 17 as a swirling flow as indicated by an arrow G. Then, the swirling flow of the saline is guided into the narrowing chamber 3 and is concentrated in the central axis direction of the swirling flow (axial concentration). The vortex is known as Rankin vortex and can concentrate the inertial force of the swirling flow near the rotating axis of the vortex.

FIG. 12 schematically illustrates a swirling speed profile of a vortex in a cross section along line XII-XII of FIG. 10. The vertical axis indicates the flow rate of the swirling flow and the value at the intersection point with the horizontal axis is 0. This means that the farther away from the origin in the vertical direction, the higher the flow rate of the swirling flow becomes. The horizontal axis indicates the distance from the center line of the mixing device 1 and the intersection point with the vertical axis is on the center line of the mixing device 1. In short, this means that the farther away from the origin in the horizontal direction is, the farther away from the center line of the mixing device 1 is.

FIG. 13 schematically illustrates a swirling speed profile of a vortex in a cross section along line XIII-XIII of FIG. 10. Like FIG. 12, the vertical axis indicates the flow rate of the swirling flow and the horizontal axis indicates the distance from the center line of the mixing device 1.

As understood from the comparison between FIG. 12 and FIG. 13, the peak of the flow rate of the swirling flow in the narrowing chamber 3 is closer to the center line of the mixing device 1 than the peak of the flow rate of the swirling flow in the swirling flow generating chamber 2. This is because the swirling flow is concentrated in the central axis direction of the vortex, namely, in a direction of the center line of the mixing device 1. The closer to the outflow opening 16 of the mixing device 1 is, the closer to the center line of the mixing device 1 the position where the flow rate of the swirling flow is maximum is.

As illustrated in FIG. 10, the jet stream of the contrast agent collides with the swirling flow of saline in the swirling flow generating chamber 2. Then, the swirling flow starts to form a swirling motion so as to entrain the jet stream from the surrounding. Afterward, as advancing to the narrowing chamber 3, the peak of the swirling strength of the swirling flow transits so as to be close to the central axis of the mixing device 1 from the outer circumferential side of the swirling flow generating chamber 2. Then, the jet stream is guided and entrained into the center of the vortex of the swirling flow with focused swirling strength.

This applies a strong rotational force to the contrast agent which is a fluid with a high viscosity, and thus centrifugal force is generated. As a result, the contrast agent splashes in an outer circumferential direction of the swirling flow generating chamber 2. This flow structure is continuously formed during injection process. As a result, turbulent flow occurs in the entire flow field in the mixing device 1. Subsequently, the flow of the mixed drug solution of the contrast agent and the saline is rectified in the narrowing chamber 3. Then, the rectified mixed drug solution is supplied from the outflow opening 16 to the third tube 303.

The mixed drug solution of the contrast agent and the saline is guided into the narrowing chamber 3 continuously narrowed toward the outflow opening 16, and two fluids each with a different vector collide positively with each other. This allows the contrast agent to be entrained in the center of the vortex and to continuously splash in an outer circumferential direction of the swirling flow generating chamber 2. As a result, turbulent flow occurs in the entire flow field and the contrast agent and the saline are efficiently mixed.

The jet stream of the contrast agent is introduced in a direction parallel to the rotating axis of the swirling flow of the saline. As a result, the swirling flow and the jet stream collide positively with each other. Thus, turbulent flow of the contrast agent which is a fluid with a high specific gravity and a high viscosity is generated and the contrast agent can be efficiently mixed three dimensionally in the mixing device 1. As a result, the mixing efficiency increases remarkably than the two-dimensional mixing. In the following description, such a stereoscopic mixing is referred to as a three-dimensional mixing.

Even for a small amount of contrast agent and saline, a vortex can be generated in several tens milliseconds. Therefore, according to the spiral flow using the mixing device 1 of the present invention, the contrast agent and the saline can be mixed in a short time and a small amount of contrast agent and saline can be reliably mixed. As a result, the present invention can exert effects of preventing unevenness from occurring in an image.

The mixing device 1 of the present invention can exert a mixing efficiency higher than that of the T-shaped joint under a wide condition that the total flow volume of contrast agent and saline is 0.6 to 10 mL/sec. Furthermore, the mixing device 1 can exert a high mixing efficiency under a condition that the flow volume of the contrast agent is higher than the flow volume of the saline, for example, under a condition that the flow volume of the contrast agent is four times the flow volume of the saline, or under a condition of short injection time, for example, under a condition that the injection time is five seconds.

FIG. 14 is a series of images obtained by actually imaging the mixed state of the contrast agent and the saline using the mixing device 1 in the present invention. FIG. 15 is a series of images obtained by imaging the mixed state of the contrast agent and the saline using the T-shaped joint. The elapsed time is shown in seconds at the upper right hand corner of each image.

The series of images in FIGS. 14 and 15 are taken by a laser induced fluorescence (LIF) method. More specifically, first, a fluorescent dye (rhodamine B) is mixed to the contrast agent. Then, an Nd:YLF laser (with a wavelength of 532 nm) is used to produce a fluorescent color and the contrast agent and the saline are injected at a 1:1 ratio. The flow volume is 3 ml/sec.

The mixing state is imaged by 500 frames per second using a high-speed camera. The image taken is converted to a monochrome image. Therefore, the portion appearing white in FIGS. 14 and 15 is the flow of the contrast agent and the portion appearing black is the flow of the saline. Thus, the degrees of mixing can be visualized by tracking the fluorescent dye.

As understood from FIG. 14, in the case of the spiral flow using the mixing device 1 in the present invention, the contrast agent and the saline are almost completely mixed in several tens milliseconds by three-dimensional mixing. Therefore, the mixed drug solution discharged from the outflow opening 16 is not separated into two layers and appears white and cloudy. Meanwhile, in the case of the two-dimensional mixing using the T-shaped joint in FIG. 15, the saline diverges at the downstream of the T-shaped joint and the drug solution is separated into two layers. Therefore, the mixing is limited in the surface where the contrast agent contacts the saline. As a result, the drug solution discharged from the outflow opening is clearly divided into white and black, which means that the mixing is not sufficiently performed.

By referring to FIG. 16, a first embodiment of the present invention will be described. The same reference numerals or characters are assigned to the same components as that of the above example, and the description is omitted.

In the example in FIG. 7, a corner portion 30 includes the curved inner surface 17 of the swirling flow generating chamber 2 and the inside end surface 11B on the first inflow opening 14 side. Air bubbles are likely to be attached to such a corner portion. Further, the large the change in angle in the corner portion is, the more the resistance increases. In light of this, in the first embodiment in FIG. 16, a taper portion 31 is formed between the curved inner surface 17 of the swirling flow generating chamber 2 and the inside end surface 11B on the first inflow opening 14 side. Thus, air bubbles are unlikely to be attached to the inner surface of the swirling flow generating chamber 2 and the resistance can be reduced.

By referring to FIG. 17, a second embodiment of the present invention will be described. The same reference numerals or characters are assigned to the same components as that of the above example, and the description is omitted.

In the example in FIG. 7, there is a corner portion 32 at the boundary C between the swirling flow generating chamber 2 and the narrowing chamber 3. In light of this, in the second embodiment, the inner surface of the narrowing chamber 3 has a streamlined shape and a smooth curved surface 33 is provided in a boundary portion between the swirling flow generating chamber 2 and the narrowing chamber 3. Further, a curved portion 34 is formed in a boundary between the curved inner surface 17 of the swirling flow generating chamber 2 and the inside end surface 11B of the first inflow opening 14 side. Thus, air bubbles are unlikely to be attached and the resistance reduces. In the second embodiment of FIG. 17, the boundary between the swirling flow generating chamber 2 and the narrowing chamber 3 outside the mixing device 1 is also formed into a smooth curved surface. However, like the above example, the boundary outside the swirling flow generating chamber 2 and the narrowing chamber 3 may be formed into a corner portion.

By referring to FIG. 18, a third embodiment of the present invention will be described. The same reference numerals or characters are assigned to the same components as that of the above example, and the description is omitted.

In the example in FIG. 7, the narrowing chamber 3 has an outer shape of a funnel and the swirling flow generating chamber 2 has an outer shape of a cylinder. In order to manufacture the mixing device 1 having different outer shapes by molding, a mold having a complicated shape needs to be prepared, which increases manufacturing costs. Further, when the mixing device 1 is manufactured by cutting the base material, the amount of cut base material increases, and thus it takes time to manufacture.

In light of this, in the third embodiment of FIG. 18, the curved side surface outside the swirling flow generating chamber 2 extends up to the narrowing chamber 3 and the third conduit pipe portion 6. More specifically, the swirling flow generating chamber 2, the narrowing chamber 3, and the third conduit pipe portion 6 shares a curved side surface 35. In other word, the swirling flow generating chamber 2, the narrowing chamber 3, and the third conduit pipe portion 6 have the cylindrical outer shape. Thus, when the mixing device 1 is manufactured by molding, the mold shape can be simplified. Further, when the mixing device 1 is manufactured by cutting the base material, the amount of cut base material can be reduced.

The mixing tube 300 in the present invention may include an optical sensor, an ultrasonic sensor, a capacitance sensor, or the like as an air detector detecting air bubbles inside first tube 301, the second tube 302, the third tube 303 or the mixing device 1. For example, when an air detector is provided outside the mixing device 1, an attaching portion for attaching the air detector may be formed on an outer surface of the mixing device 1.

By referring to FIG. 19, a fourth embodiment of the present invention will be described. The same reference numerals or characters are assigned to the same components as that of the above example, and the description is omitted.

In the example in FIG. 7, the swirling flow generating chamber 2, the narrowing chamber 3, the first conduit pipe portion 4, the second conduit pipe portion 5, and the third conduit pipe portion 6 are integrally made of the same member. The first inflow opening 14, the second inflow opening 15 and the outflow opening 16 having a narrower inner diameter than that of the swirling flow generating chamber 2 and the narrowing chamber 3 are required to have strength higher than that of the swirling flow generating chamber 2 and the narrowing chamber 3. In light of this, in the fourth embodiment of FIG. 19, the first conduit pipe portion 4 having the first inflow opening 14, the second conduit pipe portion 5 having the second inflow opening 15, and the third conduit pipe portion 6 having the outflow opening 16 are made of members 36, 37, and 38 respectively each independent from the swirling flow generating chamber 2 and the narrowing chamber 3.

The first conduit pipe portion 4 is made of an independent member 36, the second conduit pipe portion 5 is made of an independent member 37, and the third conduit pipe portion 6 is made of an independent member 38. Thus, the first conduit pipe portion 4, the second conduit pipe portion 5, and the third conduit pipe portion 6 can be made of a material with strength higher than that of the swirling flow generating chamber 2 and the narrowing chamber 3. The first conduit pipe portion 4, the second conduit pipe portion 5, and the third conduit pipe portion 6 can be connected to the swirling flow generating chamber 2 and the narrowing chamber 3 by bonding, threaded connection, or the like.

The mixing device 1 in the fifth embodiment of the present invention may be arranged such that the mixing device 1 is arranged vertically upright or inclined obliquely so that the outflow opening 16 is located below the first inflow opening 14. Such an arrangement allows the central axis line of the first inflow opening 14, the swirling flow generating chamber 2 and the narrowing chamber 3 to be parallel to the gravitational direction or to be inclined to the gravitational direction. In other word, the central axis line of the first inflow opening 14, the swirling flow generating chamber 2 and the narrowing chamber 3 is orthogonal or inclined to the floor surface. The flow direction A (FIG. 7) of the mixed drug solution is oriented in the gravitational direction.

Thus, in the mixing device 1, the orientation of the flow direction A of the mixed drug solution in the gravitational direction increases the axisymmetry of the system of the mixed drug solution in the mixing device 1. Therefore, even if the drug solutions to be mixed are greatly affected by specific gravity, the drug solutions can be effectively mixed. More specifically, even if the drug solutions to be mixed have a large difference in specific gravity or even if the drug solutions to be mixed are relatively greatly affected by specific gravity because the drug solutions to be mixed have a small inertial force (low swirling speed), the drug solutions can be effectively mixed.

In order to arrange the mixing device 1 as described above, the mixing device 1 may be fixed to the drug solution injecting apparatus 200 parallel to the gravitational direction. In addition, a relay stand may be interposed between the drug solution injecting apparatus 200 and the patient, and the mixing device 1 is fixed to the relay stand parallel to the gravitational direction. Further, the first tube 301 and the second tube 302 may be a rigid tube with a shape bent toward the floor surface and the mixing device 1 is held parallel to the gravitational direction. In addition to the above, the first tube 301 and the second tube 302 may be made sufficiently long so that the mixing tube 300 hangs toward the floor surface from the drug solution injecting apparatus 200, and the mixing device 1 is held parallel to the gravitational direction.

Various modifications can be made to the mixing device within the scope of the present invention. For example, in order to reduce the resistance to the discharged mixed drug solution, the inner diameter of the outflow opening 16 may be larger than that of the first inflow opening 14. Further, in order to secure a sufficient volume, the length of the swirling flow generating chamber 2 along the central axis line of the swirling flow generating chamber 2 may be made longer than the length of the narrowing chamber 3.

The above example focuses on the case in which two kinds of drug solutions of the contrast agent and the saline are mixed. However, one of the two kinds of drug solutions may be the mixed drug solution of the contrast agent and the saline, and the other may be saline. In this case, instead of the contrast agent, the first syringe 201 is filled with the mixed drug solution of the contrast agent and the saline. The second syringe 202 is filled with the saline. The specific gravity and viscosity of this mixed drug solution are higher than those of the saline.

The present invention has been described using the above example and each embodiment, but the present invention is not limited to the configurations of the above example and each embodiment. The present invention includes modifications of the components of the present invention and the configuration equivalent to the components of the present invention within the scope of the invention claimed in the claims. Further, the above example and each embodiment can be appropriately combined without substantially changing the content of the present invention.

This application claims priority from Japanese Patent Application No. 2010-87017 filed on Apr. 5, 2010, which is hereby incorporated by reference herein.

The invention claimed is:

1. A drug solution mixing method comprising:
preparing a mixing device having an outflow opening from which a mixed drug solution is discharged, a narrowing chamber having a space continuously narrowed toward the outflow opening, and a swirling flow generating chamber;
arranging the mixing device so that the outflow opening is located below the swirling flow generating chamber in a gravitational direction and a central axis line of the swirling flow generating chamber and the narrowing chamber is parallel to the gravitational direction or is inclined to the gravitational direction;
generating a swirling flow of a second drug solution in the swirling flow generating chamber by introducing the second drug solution into the swirling flow generating chamber through a second inflow opening formed on the swirling flow generating chamber;
directly introducing a first drug solution into the swirling flow generating chamber through a first inflow opening, which is formed on an end surface of the swirling flow generating chamber, in a direction parallel to a central axis of the swirling flow;
guiding the first drug solution and the second drug solution into the space in the narrowing chamber to mix the first drug solution and the second drug solution; and
discharging the mixed drug solution of the first drug solution and the second drug solution from the outflow opening.

2. The drug solution mixing method according to claim 1, wherein the first drug solution is a contrast agent and the second drug solution is saline.

3. The drug solution mixing method according to claim 1, wherein the first drug solution is introduced into the swirling flow from above the second drug solution.

4. The drug solution mixing method according to claim 1, wherein the mixing device is arranged so as to be fixed to a drug solution injecting apparatus having a head to which a first syringe filled with the first drug solution and a second syringe filled with the second drug solution are attached.

5. The drug solution mixing method according to claim 1, wherein the mixing device is arranged so as to be fixed to a relay stand which is placed between a patient and a drug solution injecting apparatus having a head to which a first syringe filled with the first drug solution and a second syringe filled with the second drug solution are attached.

6. The drug solution mixing method according to claim 1, wherein the mixing device is arranged so as to be held with a tube which is communicated with the mixing device.

7. The drug solution mixing method according to claim 6, wherein the tube is a rigid tube with a shape bent downward.

8. The drug solution mixing method according to claim 1, wherein the second inflow opening is formed on a side surface of the swirling flow generating chamber and located downstream from the first inflow opening.

9. A drug solution injecting system comprising:
a mixing device having an outflow opening from which a mixed drug solution is discharged, a narrowing chamber which has a space continuously narrowed toward the outflow opening, and a swirling flow generating chamber; and
a fixing member to which the mixing device is fixed so that the outflow opening is located below the swirling flow generating chamber in a gravitational direction and a central axis line of the swirling flow generating chamber and the narrowing chamber is parallel to the gravitational direction or is inclined to the gravitational direction,
wherein the mixing device has a first inflow opening formed on an end surface of the swirling flow generating chamber so as to directly introducing a first drug solution into the swirling flow generating chamber, and a second inflow opening formed on the swirling flow generating chamber so as to introduce a second drug solution into the swirling flow generating chamber.

10. The drug solution injecting system according to claim 9, the fixing member is a drug solution injecting apparatus having a head to which a first syringe filled with a first drug solution and a second syringe filled with a second drug solution are attached, or is a relay stand which is placed between a patient and the drug solution injecting apparatus.

11. The drug solution injecting system according to claim 9, wherein the second inflow opening is formed on a side surface of the swirling flow generating chamber and located downstream from the first inflow opening.

12. A drug solution injecting system comprising:
a mixing device having an outflow opening from which a mixed drug solution is discharged, a narrowing chamber which has a space continuously narrowed toward the outflow opening, and a swirling flow generating chamber; and a holding member which holds the mixing device so that the outflow opening is located below the swirling flow generating chamber in a gravitational direction and a central axis line of the swirling flow generating chamber and the narrowing chamber is parallel to the gravitational direction or is inclined to the gravitational direction, wherein the mixing device has a first inflow opening formed on an end surface of the swirling flow generating chamber so as to directly introducing a first drug solution into the swirling flow generating chamber, and a second inflow opening formed on the swirling flow generating chamber so as to introduce a second drug solution into the swirling flow generating chamber.

13. The drug solution injecting system according to claim 10, the holding member is a tube which is communicated with the mixing device.

14. The drug solution mixing method according to claim 13, wherein the tube is a rigid tube with a shape bent downward.

15. The drug solution injecting system according to claim 12, wherein the second inflow opening is formed on a side surface of the swirling flow generating chamber and located downstream from the first inflow opening.

* * * * *